(12) United States Patent
Sachdeva

(10) Patent No.: US 6,587,828 B1
(45) Date of Patent: Jul. 1, 2003

(54) METHOD AND APPARATUS FOR AUTOMATED GENERATION OF A PATIENT TREATMENT PLAN

(75) Inventor: Rohit Sachdeva, Plano, TX (US)

(73) Assignee: Ora Metrix, Inc., Dallas, TX (US)

( * ) Notice: Subject to any disclaimer, the term of this patent is extended or adjusted under 35 U.S.C. 154(b) by 0 days.

(21) Appl. No.: 09/452,033

(22) Filed: Nov. 30, 1999

(51) Int. Cl.⁷ .............................................. G06F 17/60
(52) U.S. Cl. ..................................................... 705/1
(58) Field of Search ............................................ 705/1

(56) References Cited

U.S. PATENT DOCUMENTS

| | | | |
|---|---|---|---|
| 4,489,387 A | * 12/1984 | Lamb et al. | 600/301 |
| 5,011,405 A | 4/1991 | Lemchen | 433/24 |
| 5,338,198 A | 8/1994 | Wu et al. | 433/213 |
| 5,395,238 A | 3/1995 | Andreiko et al. | 433/24 |
| RE35,169 E | 3/1996 | Lemchen | 433/24 |
| 5,518,397 A | 5/1996 | Andreiko et al. | 433/24 |
| 5,528,735 A | * 6/1996 | Strasnick et al. | 345/427 |
| 5,533,895 A | 7/1996 | Andreiko et al. | 433/24 |
| 5,618,176 A | 4/1997 | Andreiko et al. | 433/11 |
| 5,826,237 A | * 10/1998 | Macrae et al. | 705/2 |
| 5,879,158 A | 3/1999 | Doyle et al. | 433/24 |
| 5,975,893 A | 11/1999 | Chishti et al. | 433/6 |
| 6,014,629 A | * 1/2000 | DeBruin-Ashton | 705/14 |
| 6,063,028 A | * 5/2000 | Luciano | 128/898 |
| 6,068,482 A | 5/2000 | Snow | 433/223 |
| 6,099,314 A | 8/2000 | Kopelman et al. | 433/213 |
| 6,217,325 B1 | 4/2001 | Chishti et al. | 433/24 |
| 6,227,850 B1 | 5/2001 | Chishti et al. | 433/24 |
| 6,227,851 B1 | 5/2001 | Chishti et al. | 433/24 |
| 6,236,878 B1 | * 5/2001 | Taylor et al. | 128/920 |

FOREIGN PATENT DOCUMENTS

WO    WO 9901832 A1 *   1/1999 ........... G06F/17/60

OTHER PUBLICATIONS

Muilenberg, T. "Patient Activities Planning and Progress—A Humanistic Integrated Team Approach," American Health Care Association Jnl., v4, n2, p46–52, Mar. 1978.*
Bisby, Adam, "Health care market goes the distance." Computer Dealer News, Aug. 10, 1998.*
Co–pending U.S. patent application of Rohit Sachdeva, Ser. No. 09/560,647 filed Apr. 28, 2000.*

* cited by examiner

*Primary Examiner*—John G. Weiss
*Assistant Examiner*—Jonathan Ouellette
(74) *Attorney, Agent, or Firm*—McDonnell Boehnen Hulbert & Berghoff

(57) ABSTRACT

A method and apparatus for generating a patient treatment plan includes processing that begins by providing a list of health care services to a patient and/or care provider. The processing continues by prompting for input of digital information regarding the patient when a health care service has been selected. The processing continues by determining whether a sufficient amount of digital information has been received. If so, the processing continues by simulating treatment of a patient based on the digital information, a treatment objective, and normalized patient data. The processing then continues by generating the patient treatment plan in accordance with the simulating of the treatment when the simulated treatment results have been acknowledged.

32 Claims, 5 Drawing Sheets

METHOD AND APPARATUS FOR AUTOMATED GENERATION OF A PATIENT TREATMENT PLAN

TECHNICAL FIELD OF THE INVENTION

This invention relates generally to the practice of orthodontics and in particular to a method and apparatus for treating an orthodontic patient.

BACKGROUND OF THE INVENTION

Orthodontics is the practice of manipulating a patient's teeth to provide better function and appearance. In general, brackets are bonded to a patient's teeth and coupled together with an arched wire. The combination of the brackets and wire provide a force on the teeth causing them to move. Once the teeth have moved to a desired location and are held in a place for a certain period of time, the body adapts bone and tissue to maintain the teeth in the desired location. To further assist in retaining the teeth in the desired location, a patient may be fitted with a retainer.

To achieve tooth movement, orthodontists utilize their expertise to first determine a three-dimensional mental image of the patient's physical orthodontic structure and a three-dimensional mental image of a desired physical orthodontic structure for the patient, which may be assisted through the use of x-rays and/or models. Based on these mental images, the orthodontist further relies on his/her expertise to place the brackets and/or bands on the teeth and to manually bend (i.e., shape) wire, such that a force is asserted on the teeth to reposition the teeth into the desired physical orthodontic structure. As the teeth move towards the desired location, the orthodontist makes continual judgments as to the progress of the treatment, the next step in the treatment (e.g., new bend in the wire, reposition or replace brackets, is head gear required, etc.), and the success of the previous step.

In general, the orthodontist makes manual adjustments to the wire and/or replaces or repositions brackets based on his or her expert opinion. Unfortunately, in the oral environment, it is impossible for a human being to accurately develop a visual three-dimensional image of an orthodontic structure due to the limitations of human sight and the physical structure of a human mouth. In addition, it is humanly impossible to accurately estimate three-dimensional wire bends (with an accuracy within a few degrees) and to manually apply such bends to a wire. Further, it is humanly impossible to determine an ideal bracket location to achieve the desired orthodontic structure based on the mental images. It is also extremely difficult to manually place brackets in what is estimated to be the ideal location. Accordingly, orthodontic treatment is an iterative process requiring multiple wire changes, with the process success and speed being very much dependent on the orthodontist's motor skills and diagnostic expertise. As a result of multiple wire changes, patient discomfort is increased as well as the cost. As one would expect, the quality of care varies greatly from orthodontist to orthodontist as does the time to treat a patient.

As described, the practice of orthodontics is very much an art, relying on the expert opinion and judgment of the orthodontist. In an effort to shift the practice of the orthodontic from an art to a science, many innovations have been developed. For example, U.S. Pat. No. 5,518,397 issued to Andreiko, et. al, describes a method of forming an orthodontic brace. Such a method includes obtaining a model of the teeth of a patient's mouth and a prescription of desired positioning of such teeth. The two-dimensional contour of the teeth of the patient's mouth is determined from the model. Calculations of the contour and the desired positioning of the patient's teeth are then made to determine the geometry of an orthodontic appliance (e.g., grooves or slots to be provided in the brackets to be provided. Custom brackets including a special geometry have been created for receiving an arch wire to form an orthodontic brace system. Such geometry is intended to provide for the disposition of the arched wire on the bracket in a progressive curvature of a horizontal plane and a substantially linear configuration in a vertical plane. The geometry of the bracket is altered, (e.g., by cutting grooves into the bracket at individual positions and angles and with particular depth) and in accordance with such calculations of the geometry of the patient's teeth. In such a system, the brackets are customized to provide three-dimensional movement of the teeth once the wire, which has a two-dimensional shape, (i.e., linear shape in the vertical plane and curvature in the horizontal plane) is applied to the brackets.

Other innovations relating to bracket and bracket placements have also been patented. For example, such patent innovations are disclosed in U.S. Pat. No. 5,618,716 entitled "Orthodontic Bracket and Ligature" a method of ligating arch wires to brackets, U.S. Pat. No. 5,011,405 "Entitled Method for Determining Orthodontic Bracket Placement," U.S. Pat. No. 5,395,238 entitled "Method of Forming Orthodontic Brace," and U.S. Pat. No. 5,533,895 entitled "Orthodontic Appliance and Group Standardize Brackets therefore and methods of making, assembling and using appliance to straighten teeth".

Unfortunately, the current innovations to change the practice of orthodontic from an art to a science have only made limited progress. This limit is due to, but not restricted to, the brackets being the focal point for orthodontic manipulation. By having the brackets as the focal point, placement of each bracket on a corresponding tooth is critical. Since each bracket includes a custom sized and positioned wire retaining groove, a misplacement of a bracket by a small amount (e.g., an error vector having a magnitude of millimeter or less and an angle of a few degrees or less) can cause a different force system (i.e., magnitude of movement and direction of movement) than the desired force system to be applied to the tooth. As such, the tooth will not be repositioned to the desired location.

Another issue with the brackets being the focal point is that once the brackets are placed on the teeth, they are generally fixed for the entire treatment. As such, if the treatment is not progressing as originally calculated, the orthodontist uses his or her expertise to make the appropriate changes. The treatment may not progress as originally calculated for several reasons. For example, misplacement of a bracket, misapplication of a bend in the wire, loss or attrition of a bracket, bonding failure, the patient falls outside of the "normal" patient model (e.g., poor growth, anatomical constraints, etc.), patient lack of cooperation in use of auxiliary appliance, etc. are factors in delayed treatment results. When one of these conditions arise, the orthodontist utilizes his or her expertise to apply manual bends to the wire to "correct" the errors in treatment. Thus, after the original scientific design of the brackets, the practice of the orthodontic converts back to an art for many patients for the remainder of the treatment.

Another issue with the brackets being the focal point is that customized brackets are expensive. A customized bracket is produced by milling a piece of metal (e.g., stainless steel, aluminum, ceramic, titanium, etc.) and tumble polishing the milled bracket. While the milling process is very accurate, some of the accuracy is lost by tumble polishing. Further accuracy is lost in that the placement of the brackets on the teeth and installation of the wire are imprecise operations. As is known, a slight misplacement of one bracket changes the force on multiple teeth and hinders treatment. To assist in the placement of the custom brackets, they are usually shipped to the orthodontist in an installation jig. Such an installation jig is also expensive. Thus, such scientific orthodontic treatment is expensive and has many inherent inaccuracies.

Therefore, a need exists for a method and apparatus that provides a scientific approach to orthodontics throughout the treatment of a patient, maintains treatment costs, and provides a more consistent treatment time, especially with respect to automation of treatment plan generation.

DETAILED DESCRIPTION OF A PREFERRED EMBODIMENT

Generally, the present invention provides a method and apparatus for generating a patient treatment plan. Such a method and apparatus includes processing that begins by providing a list of health care services to a patient and/or care provider. The processing continues by prompting for input of digital information regarding the patient when a health care service has been selected. The processing continues by determining whether a sufficient amount of digital information has been received. If so, the processing continues by simulating treatment of a patient based on the digital information, a treatment objective, and normalized patient data. The processing then continues by generating the patient treatment plan in accordance with the simulating of the treatment when the simulated treatment results have been acknowledged. With such a method and apparatus, the generation of a patient treatment plan may be automated for particular types of health care services, including orthodontic care, dental care, and medical care.

Figure 1:
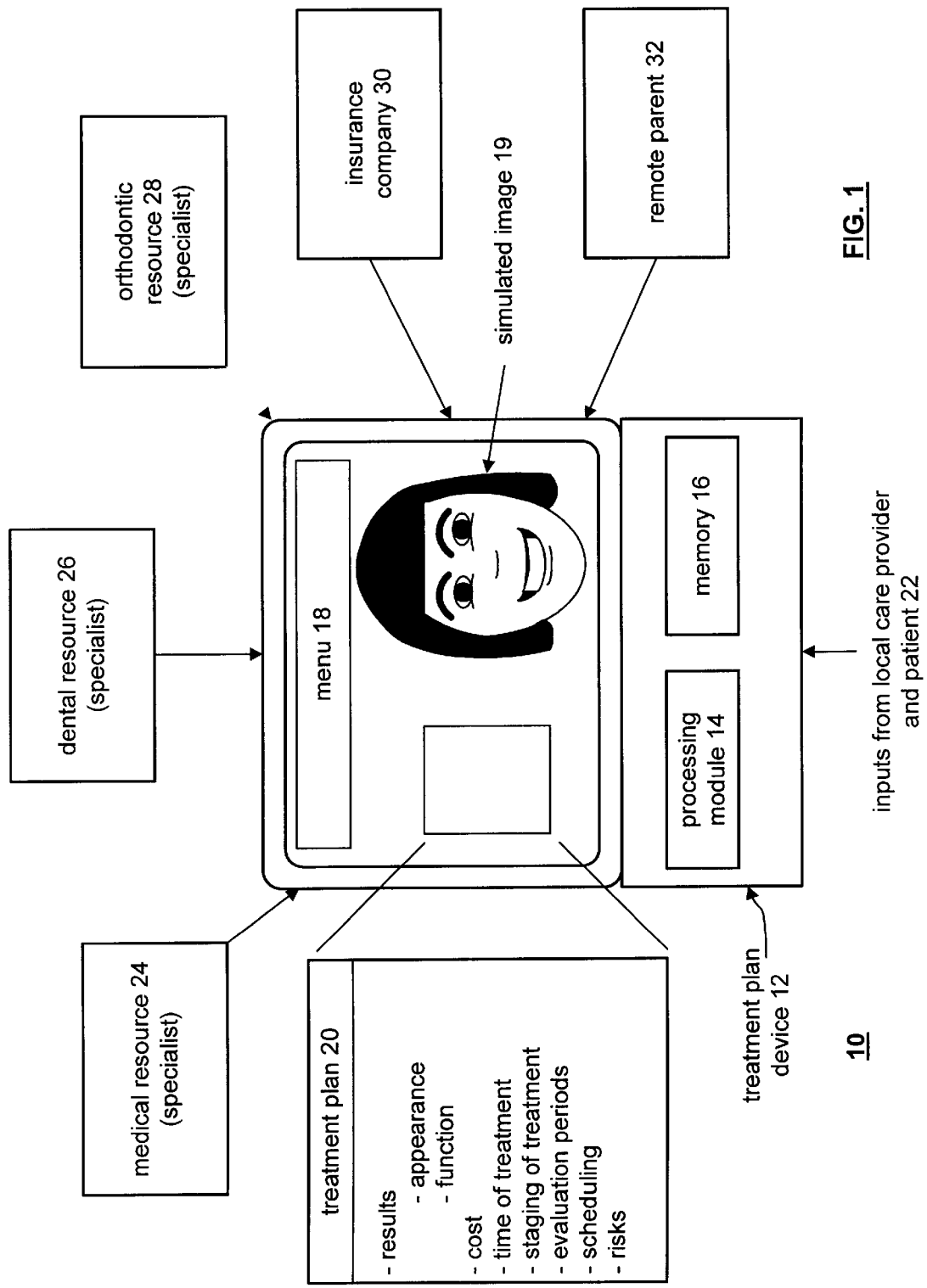
FIG. 1 illustrates a graphical diagram of a treatment plan device in accordance with the present invention.

The present invention can be more fully described with reference to FIGS. 1 through 5. FIG. 1 illustrates a graphical diagram of an orthodontic treatment system 10 that includes a treatment plan device 12. The treatment plan device 12 includes a processing module 14 and memory 16. The processing module 14 may be a single processing device or a plurality of processing devices. Such a processing device may be a microcontroller, microcomputer, microprocessor, central processing unit, a digital signal processor, state machine, logic circuitry, and/or any device that manipulates signals (e.g., analog and/or digital) based on operational instructions. The memory 16 may be a single memory device or a plurality of memory devices. Such a memory device may be a read-only memory, random access memory, floppy disk memory, flash memory, and/or any device that stores operational instructions. Note that when the processing module implements one or more functions via a state machine and/or logic circuitry, the memory storing the corresponding operational instructions is embedded within the circuitry comprising the state machine and/or logic circuitry.

The treatment plan device 12 is operably coupled to receive inputs from a local care provider and/or a patient 22. Such inputs include the digital information required to generate a treatment plan. The digital information may include one or more of: the patient's chief complaint, the patient's medical history, the patient's dental history, clinical examination, three-dimensional images of the patient's orthodontic structure, video graphic examination, functional examination information, soft tissue evaluation, skeletal evaluation, and patient's objectives. In addition, the digital information may include cost constraints based on the patient's insurance carrier and/or financial status. Further, the digital information includes the length of treatment the patient is willing to undergo, the patient's commitment level to adhering to treatment, etc.

The treatment plan device 12 includes firmware to display a menu 18 and a treatment plan 20. The treatment plan device 12 may further include firmware to display a simulated image 19, or exterior appearance model. The menu 18 may include the list of health care services such as dental services, orthodontic services, and/or medical services, a list of orthodontic products (e.g., tooth paste, floss, etc.), and/or resources of orthodontic information (e.g., factual information, care, etc.). The patient and/or care provider selects from one of these health care categories and is subsequently provided with a menu that offers selection of one of well-care, health care, and/or follow-up care. Note that the health care category may further be divided into acute or chronic ailments where a series of prompts are provided in accordance with such information. For example, if a patient has selected health care and the situation is acute, the treatment plan device 12 may automatically call 911. As such, via the treatment plan device 12, the patient with or without the assistance of a local care provider can initiate the generation of a treatment plan for him or herself. Further note that the well-care category provides a list of options for well-care treatment. For example, the well-care category for orthodontic patients may include information on re-installing an arch wire, list of foods that should be avoided, brushing and flossing advise, etc.

To facilitate the generation of the treatment plan 20, the treatment plan device 12 may interface with a medical resource 24, a dental resource 26, an orthodontic resource 28, an insurance company 30, other resources (not shown), and/or a remote parent 32. Based on input from one or more of these sources and the inputs provided by the patient and/or local care provider, the treatment plan device 12 generates the treatment plan 20. The treatment plan will include results, which may be based on appearance and/or function, costs of treatment, time for treatment, staging of treatment events, evaluation periods, scheduling, and associated risks. Note that the scheduling may be done via the Internet or other mechanism. Further note that the medical resource 24, the dental resource 26, and the orthodontic resource 28 may be local to the treatment plan device, (i.e., coupled via a local area network), or may be remotely coupled through a wide area network and/or the Internet. Further note that the treatment plan device may be included in a site orthodontic system and/or an orthodontic server as described in patent application Ser. No. 09/451,637, entitled METHOD AND APPARATUS FOR DETERMINING AND MONITORING ORTHODONTIC TREATMENT, in patent application Ser. No. 09/451,560, entitled METHOD AND APPARATUS FOR TREATING AN ORTHODONTIC PATIENT, and in a patent application Ser. No. 09/452,038, entitled METHOD AND APPARATUS FOR SITE TREATMENT OF AN ORTHODONTIC PATIENT. Each of these patent applications has a filing date the same as the present application and is assigned to the same assignee as the present invention.

Figure 2:
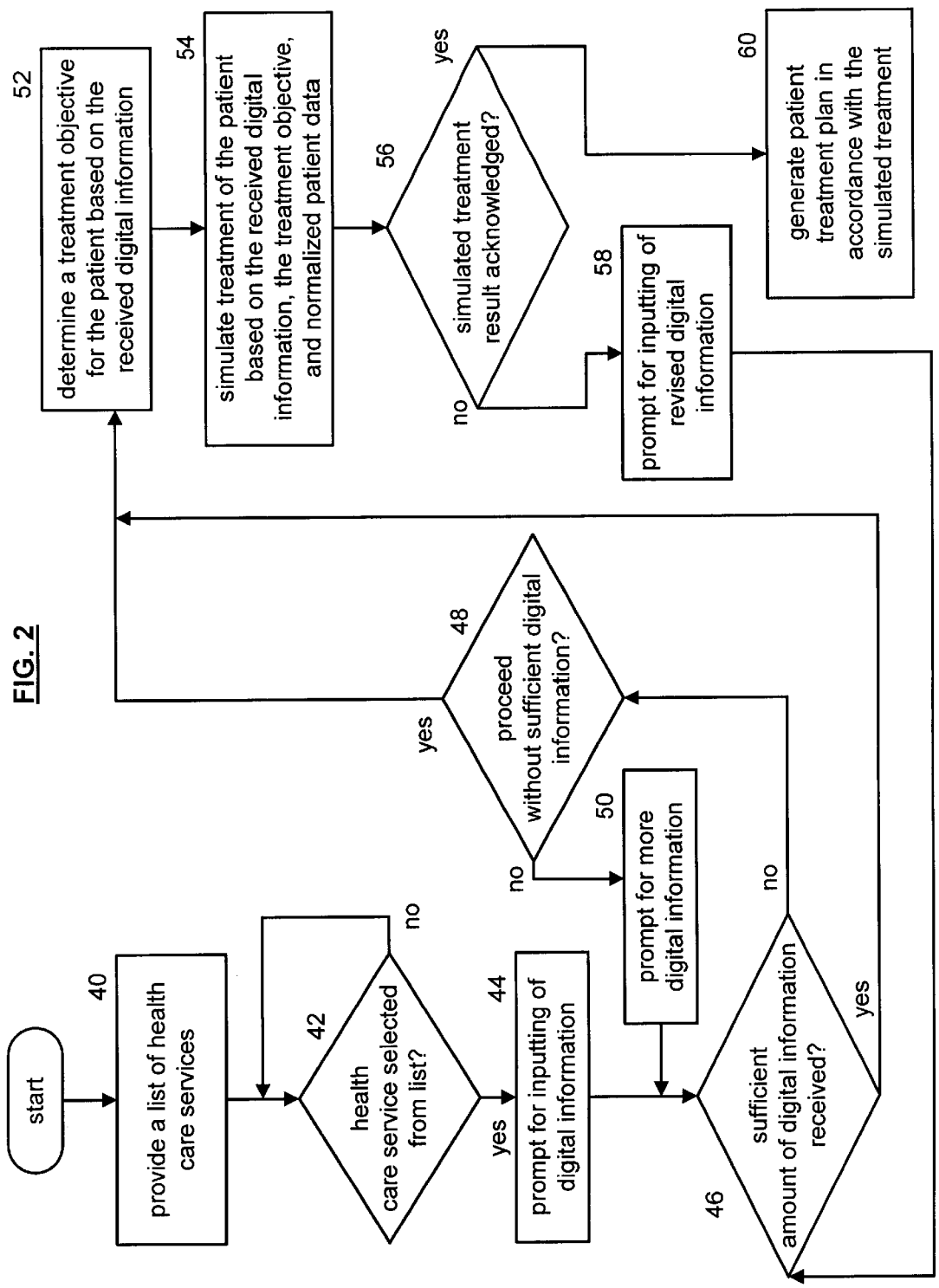
FIG. 2 illustrates a logic diagram of a method for generating a patient treatment plan in accordance with the present invention.

FIG. 2 illustrates a logic diagram of a method for generating a patient treatment plan for a patient who is just beginning treatment or has received some treatment. The steps of FIG. 2 may be implemented as operational instructions and executed by processing module 14 and stored in memory 16 of the treatment plan device 12. The process begins at step 40 where a list of health care services is provided. The list of health care services is provided on screen to a patient and/or local care provider. The display provided may be a graphical user interface that includes graphics, text, voice inputs, or a combination thereof that allow the patient and/or local service care provider to select one or more of the health care services. The list of health care services may include orthodontic services, dental services, and/or cosmetic medical services, which may be inter disciplinary or multi-disciplinary. Each of these service categories may include subcategories as well. For example, the subcategories may include well-care treatment, emergency treatment, chronic treatment, and/or follow-up treatment in a limited or comprehensive manner.

The process then proceeds to step 42 where a determination is made as to whether a health care service has been selected from the list. Once the health care service has been selected, the process proceeds to step 44 where a prompt is provided that requests the user (i.e., the patient and/or local health care provider) to input digital information regarding the patient. For example, the digital information of an orthodontic patient includes a digital model of the patient's malocclusion, patient's chief compliant, patient's demands, financial constraints, treatment length, desired orthodontic function, desired orthodontic appearance, the patient's dental history, the patient's medical history, and/or acceptable deviations. In addition, the digital information may include normalized patient data that includes orthodontic parameters relating to the patient. The normalized patient data may be retrieved from a database of orthodontic parameters as described in the above listed patent applications.

The process then proceeds to step 46 where a determination is made as to whether a sufficient amount of data has been received. Of the digital information previously described, some information is essential for determining a treatment plan while other pieces of data are peripheral to treatment. For example, a digital model of the patient's malocclusion, the patient's personal information (e.g., age, sex, race, etc.) and the desired orthodontic results are essential. Other information such as treatment length, financial constraints, the patient's dental history, the patient's medical history, and acceptable deviations may be peripheral information. As such, at step 46 a determination is made as to whether the essential information has been received.

If a sufficient amount of data has not been received, the process proceeds to step 48 where a determination is made as to whether the process is to proceed without the sufficient digital information. If not, the process proceeds to step 50 where a prompt is provided requesting more digital information. Note that, at step 48, the patient and/or local service care provider may request that the process proceed without further digital information.

When a sufficient amount of digital information has been received, or it has been determined that the process will proceed without sufficient digital information, the process proceeds to step 52. At step 52, a treatment objective is determined for the patient based on the received digital information. The treatment objective may include one or more of dental appearance, orthodontic function, facial appearance, skeletal appearance and/or function, treatment time, patient's commitment to treatment, costs, etc. The process then proceeds to step 54 where treatment of the patient is simulated based on the received digital information, the treatment objective, and normalized patient data. For a more detailed discussion of the simulation of treatment refer to patent application Ser. No. 09/452,031, entitled METHOD AND APPARATUS FOR GENERATING A DESIRED THREE-DIMENSIONAL IMAGE OF AN IDEAL ORTHODONTIC STRUCTURE, and a filing date the same as the present patent application, and is assigned to the same assignee as the present invention.

The process then proceeds to step 56 where a determination is made as to whether the patient and/or local care provider has acknowledged the simulated treatment results. In other words, has the patient and/or local care provider approved of the simulated treatment results. If not, the process proceeds to step 58 where a prompt requests further digital information and/or requests the user to revise the digital information already provided. The process then reverts to step 46.

If the simulated treatment results have been acknowledged, the process proceeds to step 60. At step 60, the patient treatment plan is generated in accordance with the simulated treatment. The treatment plan will include precise steps for treating the patient from the patient's initial condition to the desired results. Accordingly, for an orthodontic patient, the treatment plan will include the time of treatment, a series of wires to support the treatment, bracket placement, patient care requirements, scheduling of patient visits and/or adjustments, monitoring progress to provide feedback for adjusting the treatment plan when necessary. In addition, the treatment plan may identity patient resources (e.g., chat groups, patient care web page, etc.) that assist the patient in becoming a more informed consumer. Note that the patient and/or the local care provider may change the treatment object at any time during treatment, which would cause a new treatment plan to be generated.

Figure 3:
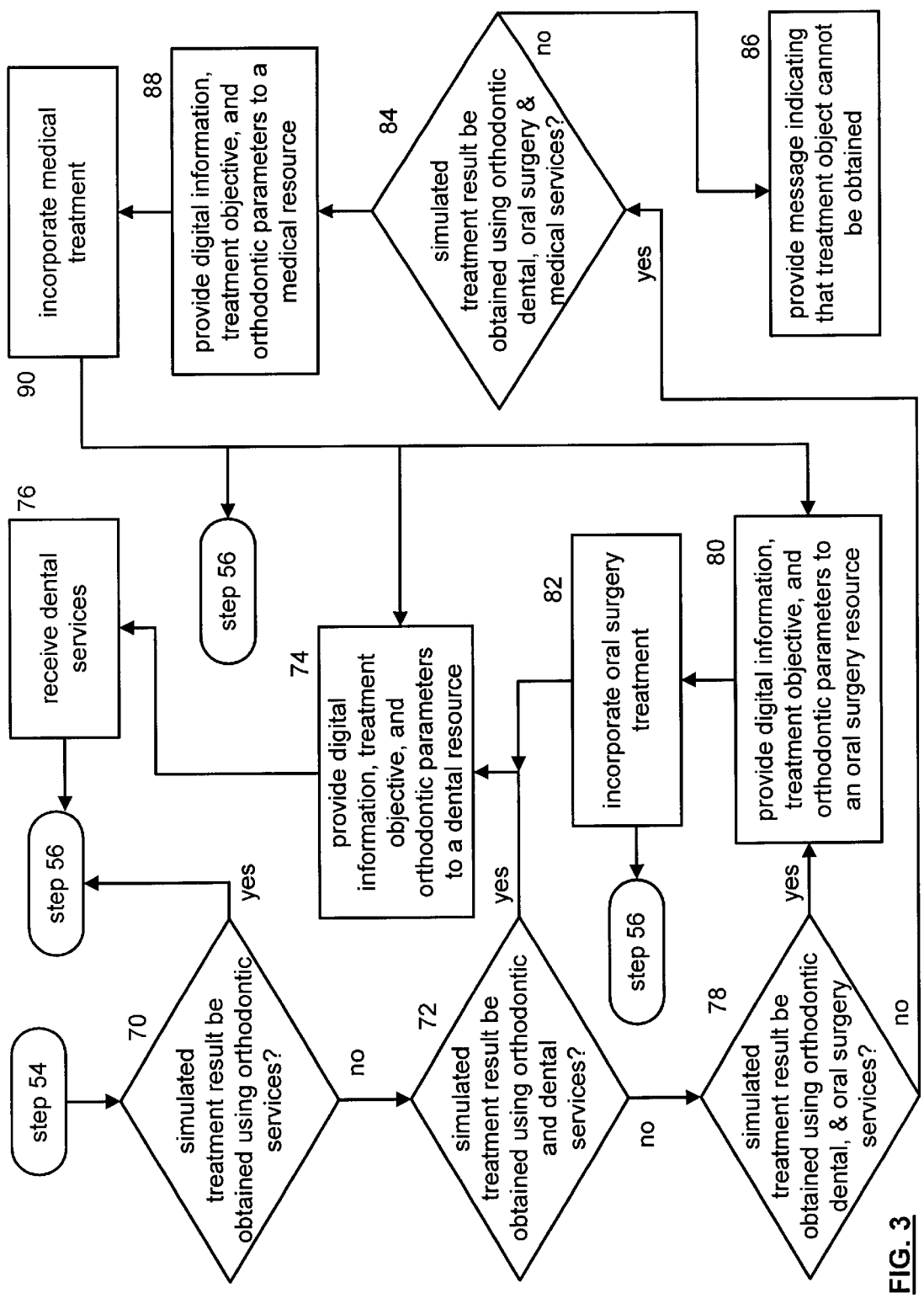
FIG. 3 illustrates a logic diagram of a method for step 54 of FIG. 2.

FIG. 3 illustrates a logic diagram of step 54 of FIG. 2. The process begins at step 70 where a determination is made as to whether the simulated treatment result can be obtained using orthodontic services, i.e., does the patient only require orthodontic treatment to obtain the desired orthodontic structure. If so, the process reverts to step 56. If not, the process proceeds to step 72 where a determination is made as to whether the simulated treatment result can be obtained using orthodontic services and dental services (e.g., the patient requires at least one tooth to be extracted prior to orthodontic treatment). If so, the process proceeds to step 74 where digital information, treatment objectives, and orthodontic parameters are provided to a dental resource. The process then proceeds to step 76 where inputs from the dental services are received (e.g., which tooth to extract, how the extraction should be done, recovery time, etc). The process then proceeds to step 56 where the treatment plan is generated in accordance with the orthodontic services and the dental services.

If at step 72, the simulated treatment result cannot be obtained using orthodontic and dental services, the process proceeds to step 78. At step 78 a determination is made as to whether a simulated treatment result can be obtained using two or more of orthodontic services, dental services, and oral surgery services (e.g., jaw extension surgery, upper arch plate separating surgery, etc.). If so, the process proceeds to step 80 where digital information, the treatment objective, and orthodontic parameters are provided to an oral surgery resource. The process then proceeds to step 82 where the oral surgery treatment is incorporated into the treatment plan. The process may then revert to steps 56 of FIG. 2 or proceed to step 74. With this option, the orthodontic services may be combined with one or more of the dental services and oral surgery services. For example, for an orthodontic patient that requires tooth extraction where at least one of the teeth is a non-erupted molar, the dental services are incorporated to extract the erupted teeth and oral surgery to remove the non-erupted molar. Further, oral surgery may be required to lengthen and/or widen the upper and/or lower jaw to provide more room for the teeth, improve the patient's physical appearance, etc.

If at step 78, the treatment plan cannot be simulated using two or more of orthodontic services, dental services, and oral surgery services, the process proceeds to step 84. At step 84, a determination is made as to whether the simulated treatment result may be obtained using one or more of orthodontic services, dental services, oral surgery services, and medical services (e.g., cosmetic surgery, medication required for the patient, etc.). Note that a patient with a pre-existing medical condition may require medication before each orthodontic treatment. If the result at step 84 was negative, the process proceeds to step 86 where a message is provided indicating that the treatment objective cannot be obtained. At this point, the user may change one or more aspects of the digital information, change the treatment objective, and/or request that the treatment be simulated with compromised results, i.e., less than optimal results.

If, however, treatment can be obtained using two or more of the orthodontic, dental, oral surgery, and/or medical services, the process proceeds to step 88. At step 88, the digital information, the treatment plan objective, and orthodontic parameters are provided to a medical resource. The process then proceeds to step 90 where the medical resources provides a medical treatment information to the treatment plan device 12, which incorporates the medical treatment into the simulated treatment plan. The process then can proceed to step 56, 80, or 74. In this manner, a patient may be treated based on orthodontic services only, or a combination of orthodontic services, dental services, oral surgery services, and medical services. For example, a patient may require medication prior to each orthodontic visit to prevent further ailments, thus the treatment plan only embodies orthodontic services and medical services. As another example, a patient may require may require tooth extraction, via dental services, oral surgery to provide a widening of the jaw, and medical treatment for medication during the orthodontic visits and general dentistry visits.

Figure 4:
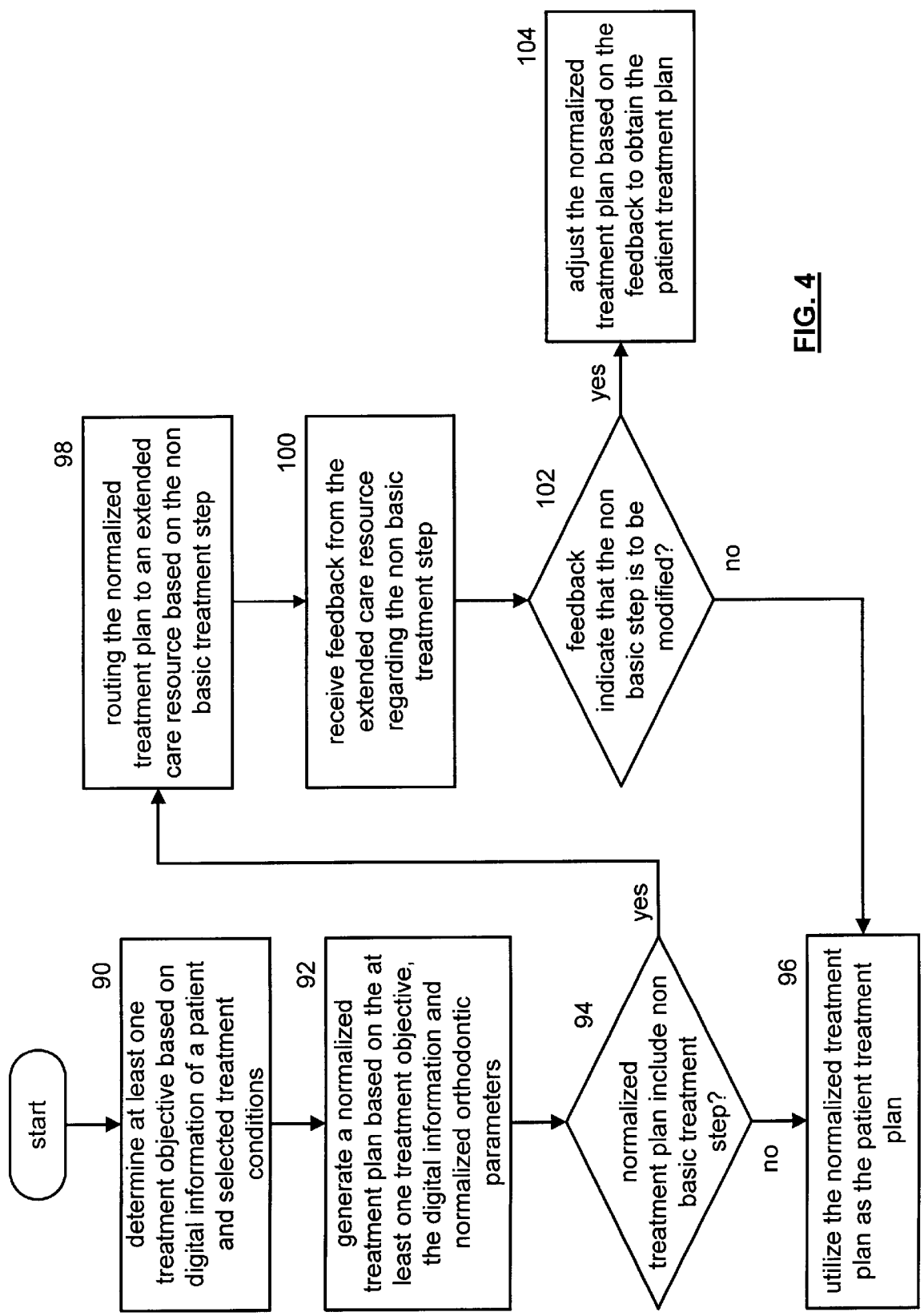
FIG. 4 illustrates a logic diagram of an alternate method for generating a patient treatment plan in accordance with the present invention.

FIG. 4 illustrates a logic diagram of an alternate method for generating a patient treatment plan. The steps of FIG. 4 may be implemented as of operational instructions that are stored in memory 16 and executed by processing module 14. Note that for processing module 14 and memory 16, they may be included in a single device or within a plurality of devices distributed throughout an orthodontic service network. For a more detailed discussion of an orthodontic service network refer to patent applications having Ser. Nos. 09/451,560, 09/452,038, and 09/451,637, which were referenced above.

The process begins at step 90 where at least one treatment objective is determined based on digital information of a patient and selected treatment conditions. Note that the treatment objective may be determined from the information received, or it may be received as an input. The selected treatment conditions may be a subset of the digital information such as costs, treatment plan, treatment time, etc. The process then proceeds to step 92 where a normalized treatment plan is generated based on at least one of the treatment objectives, the digital information and normalized orthodontic parameters. The normalized orthodontic parameters correspond to a database of information that has been obtained from patients of similar age, sex, medical conditions, and dental conditions, etc. For a more detailed discussion of orthodontic parameters refer to the patent applications having Ser. Nos. 09/451,560, 09/452,038, and 09/451,637.

The process then proceeds to step 94 where a determination is made as to whether the normalized treatment plan includes a non-basic treatment step. Note that in this method, the treatment plan is generated to optimize the patient's care and may include the suggested extraction of teeth, oral surgery, bleaching of teeth, restorative needs, periodontal surgery, and/or medical procedures. To make such a determination, therapeutic decisions regarding soft tissue modification, skeletal modification, extraction, expansion, tip back, distal molar movement, interproximal reduction, flaring, axial inclination change are factors in determining the normalized treatment plan. If the normalized treatment plan does not include a non-basic step i.e., it includes only orthodontic treatment, the process proceeds to step 96 where the normalized treatment plan is utilized as the patient treatment plan.

If, however, the normalized treatment plan includes one or more of dental services, oral surgery services, and/or medical services, the process proceeds to step 98. At step 98, the normalized treatment plan is routed to an extended care resource based on the particular non-basic treatment step. As such, the normalized treatment plan is routed to a dental resource when the normalized treatment plan includes dental services, to an oral surgery resource, when the plan includes oral surgery services, and to a medical resource, when the plan includes medical services. The process then proceeds to step 100 where feedback is received from the extended care resource regarding the non-basic treatment step. As such, the feedback regarding the step indicates whether the normalized treatment plan has accurately interpreted the corresponding non-basic treatment. Accordingly, the extended care resource is affirming or rejecting the normalized generation of the non-basic treatment step.

The process proceeds to step 102 where a determination is made as to whether the feedback indicates that the non-basic step is to be modified. If not, the process reverts to step 96. If the non-basic step is to be modified, the process proceeds to step 104 where the normalized treatment plan is adjusted based on the feedback. Having adjusted the normalized treatment plan, the patient treatment plan is obtained.

Figure 5:
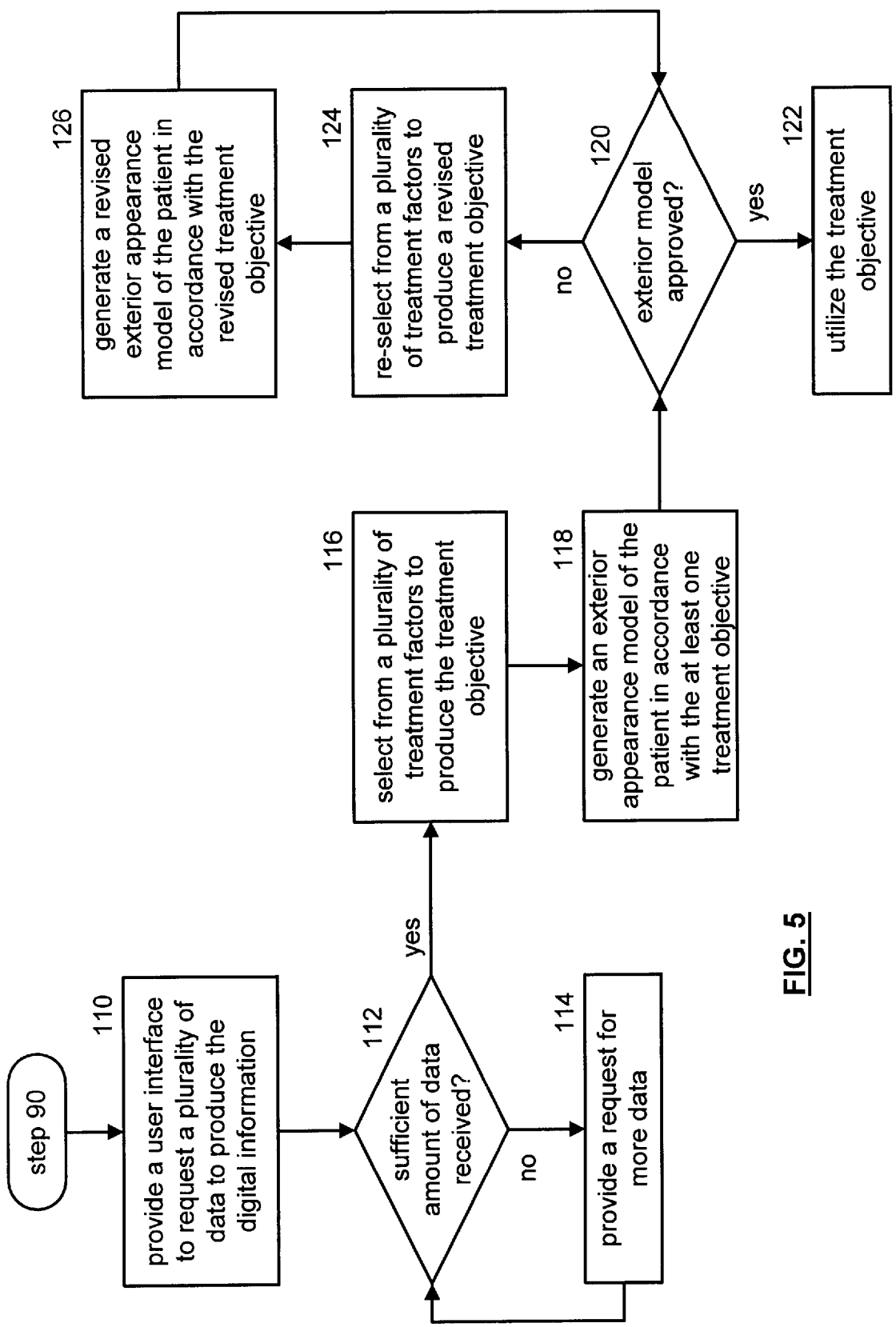
FIG. 5 illustrates a logic diagram of a method of step 90 of FIG. 4.

FIG. 5 illustrates a logic diagram for executing step 90 of FIG. 4. The process begins at step 110 where a user interface is provided to request a plurality of data, which constitutes the digital information. The process proceeds to step 112 where a determination is made as to whether a sufficient amount of data has been received. If not, the process proceeds to step 114 where a request for additional information is provided.

Once a sufficient amount of data has been received, the process proceeds to step 116. At step 116, the treatment objective is selected based on a plurality of treatment factors. Such treatment factors include patient's chief complaint, risk factors, medical and dental history, examination information, x-rays, functional examination, growth, positioning of the maxilla, positioning of the mandible, positioning of the occlusal plane, positioning of the lower incisor, positioning of the upper incisor, the lower arch form, the upper arch form, the mid-lines, arch length deficiencies, position of the upper molar, position of the lower molar, intra-arch relationships, inter-arch relationships, functional relationships, soft tissue position, care needs of the patient, and/or aesthetic relationships.

The process then proceeds to step 118 where an exterior appearance model of the patient is generated in accordance with the at least one treatment objective. The process then proceeds to step 120 where a determination is made as to whether the exterior model has been approved. If so, the process proceeds to step 122 where the treatment objective is utilized to generate the treatment plan. If not, the process proceeds to step 124 where reselection of treatment factors from a plurality of treatment factors is done to produce a revised treatment objective. The process then proceeds to step 126 where a revised exterior appearance is generated in accordance with the revised treatment objective.

The preceding discussion has presented a method and apparatus for automatically generating a treatment plan for a patient. By utilizing the automated process, a patient may receive more accurate and less expensive orthodontic treatment. In addition, the method and apparatus of the present invention provide a mechanism for converting the practice of orthodontics from an art to a science. As one of average skill in the art will appreciate, other embodiments may be derived from the teachings of the present invention without deviating from the scope of the claims.

What claimed is:

1. A method of generating an oral health care treatment plan for a patient, the method performed after the patient is in the care of a health care provider, comprising the steps of:
   a) providing a list of health care services;
   b) when a health care service is selected from the list, prompting for input of digital information regarding the patient;
   c) when at least a portion of the digital information is received, determining a treatment objective for the patient based on the received digital information;
   d) simulating treatment of the patient based on the received digital data, the treatment objective, and normalized patient data to produce a simulated treatment result; and
   e) generating the oral health care treatment plan in accordance with the simulation of the treatment when the simulated treatment results have been approved.

2. The method of claim 1, wherein step (a) further comprises providing a graphic user interface to allow for selection of the list of health care services from a category of well care treatment, emergency treatment, or follow-up treatment.

3. The method of claim 1, wherein the list of health care services includes orthodontic services, dental services, and cosmetic services.

4. The method of claim 3, wherein the digital information for orthodontics services comprises at least one of: a digital model of the patient's malocclusion, financial constraints, treatment length, desired orthodontic function, desired orthodontic appearance, the patient's dental history, the patient's medical history, and acceptable deviations.

5. The method of claim 4, wherein step (c) further comprises:
   determining whether a sufficient amount of the digital information has been received; and
   when a sufficient amount of the digital information has not been received, prompting for further disclosure of the digital information.

6. The method of claim 4, wherein the normalized patient data comprises orthodontics parameters relating to the patient and wherein step (d) further comprises:
   determining whether the simulated treatment result can be obtained using only the orthodontic services;
   when the simulated treatment result cannot be obtained using only orthodontic services, determining whether the simulated treatment result can be obtained through a combination of the orthodontic services and dental services;
   when the simulated treatment result cannot be obtained through a combination of the orthodontic services and the dental services, determining whether the simulated treatment result can be obtained through a combination of at least two of: the orthodontic services, the dental services, and oral surgery services;
   when the simulated treatment result cannot be obtained through a combination of the at least two of the orthodontic services, the dental services, and the oral surgery services, determining whether the simulated treatment result can be obtained through a combination of at least two of the orthodontic services, the dental services, the oral surgery services, and medical services; and
   when the simulated treatment result cannot be obtained through a combination of the at least two of the orthodontic services, the dental services, the oral surgery services, and the medical services, providing an indication that the treatment objectives cannot be obtained.

7. The method of claim 6 further comprises:
   when the simulated treatment result cannot be obtained using only orthodontic services, providing at least one of: the digital information, the treatment objective, and the orthodontic parameters to a dental resource;
   receiving the dental services from the dental resource;
   when the simulated treatment result cannot be obtained through a combination of the orthodontic services and the dental services, providing at least one of: the digital information, the treatment objective, and the orthodontic parameters to an oral surgery resource;
   receiving the oral surgery services from the oral surgery resource;
   when the simulated treatment result cannot be obtained through a combination of at least two of the orthodontic services, the dental services, and the oral surgery services, providing at least one of: the digital information, the treatment objective, and the orthodontic parameters to a medical resource; and
   receiving the medical services from the medical resource.

8. The method of claim 6 further comprises:
   when the simulated treatment result cannot be obtained using only the orthodontic services, providing at least one of: the digital information, the treatment objective, and the orthodontic parameters to a dental resource; and
   interacting between the dental resource and an orthodontic resource to determine that the combination of orthodontic services and dental services will provide the simulated treatment result; or interacting between the dental resource and the orthodontic resource to determine that the combination of orthodontic services and dental services will not provide the simulated treatment result.

9. The method of claim 8 further comprises:

when the simulated treatment result cannot be obtained using the orthodontic services and the dental services, providing at least one of the digital information, the treatment objective, and the orthodontic parameters to an oral surgery resource; and interacting between the dental resource, the orthodontic resource, and the oral surgery resource to determine that the combination of at least two of the orthodontic services, the dental services, and the oral surgery services will provide the simulated treatment result; or interacting between the dental resource, the orthodontic resource, and the oral surgery resource to determine that the combination of at least two of the orthodontic services, the dental services, and the oral surgery services will not provide the simulated treatment result.

10. The method of claim 9 further comprises:

when the simulated treatment result cannot be obtained using the combination of the at least two of the orthodontic services, the dental services, and the oral surgery services, providing at least one of: the digital information, the treatment objective, and the orthodontic parameters to a medical resource; and interacting between the dental resource, the orthodontic resource, the oral surgery resource, and the medical resource to determine that the combination of at least two of the orthodontic services, the dental services, the oral surgery services, and the medical services will provide the simulated treatment result; or interacting between the dental resource, the orthodontic resource, the oral surgery resource, and the medical resource to determine that the combination of the orthodontic services, the dental services, the oral surgery services, and the medical services will not provide the simulated treatment result.

11. The method of claim 6 further comprises receiving a revised treatment objective in response to the providing an indication that the treatment objectives cannot be obtained.

12. A method for generating a patient treatment plan for an orthodontic patient, the method comprises the steps of:

a) determining at least one treatment objective based on digital information of the patient and selected treatment conditions;

b) generating a normalized treatment plan based on the at least one treatment objective, the digital information and normalized orthodontic parameters;

c) determining whether the normalized treatment plan includes at least one non-orthodontic treatment step;

d) when the normalized treatment plan includes the at least one non-orthodontic treatment step, routing the normalized treatment plan to a non-orthodontic resource for evaluation based on the non-orthodontic treatment step;

e) receiving feedback from the non-orthodontic physician regarding the non-orthodontic treatment step; and f) adjusting the normalized treatment plan based on the feedback to produce the patient treatment plan when the feedback indicates that the non-orthodontic treatment step is to be modified.

13. The method of claim 12, wherein step (a) further comprises:

providing a user interface to request a plurality of data to produce the digital information;

determining whether a sufficient amount of the plurality of data has been received to produce the normalized treatment plan;

when a sufficient amount of the plurality of data has been received to produce the normalized treatment plan, selecting from a plurality of treatment factors to produce the at least one treatment objective;

generating an exterior appearance model of the patient in accordance with the at least one treatment objective; and when the exterior appearance model is approved, utilizing the at least one treatment objective.

14. The method of claim 13 further comprises:

when the exterior appearance model is not approved, re-selecting from the plurality of treatment factors to produce a revised treatment objective;

generating a revised exterior appearance model of the patient in accordance with the revised treatment objective; and when the revised exterior appearance model is approved, utilizing the revised treatment objective.

15. The method of claim 12, wherein the non-orthodontic treatment step comprises at least one of a dental service, an oral surgery service, and a medical service.

16. The method of claim 15, wherein step (d) further comprises:

routing the normalized treatment plan to a dental resource when the non-orthodontic treatment step requires the dental service;

routing the normalized treatment plan to an oral surgery resource when the non-orthodontic treatment step requires the oral surgery service; and routing the normalized treatment plan to a medical resource when the non-orthodontic treatment step requires the medical service.

17. A device for generating an oral health care treatment plan for a patient in the care of a health care provider, the device comprising:

a processing module; and memory operably coupled to the processing module, wherein the memory includes operational instructions that cause the processing module to (a) provide a list of health care services; (b) when a health care service is selected from the list, prompt for input of digital information regarding the patient; (c) when at least a portion of the digital information is received, determine a treatment objective for the patient based on the received digital information; (d) simulate treatment of the patient based on the received digital data, the treatment objective, and normalized patient data to produce a simulated treatment result; and (e) generate the oral health care treatment plan in accordance with the simulation of the treatment when the simulated treatment results have been approved.

18. The device of claim 17, wherein the memory further comprises operational instructions that cause the processing module to provide a graphic user interface to allow for selection of the list of health care services from a category of well care treatment, emergency treatment, or follow-up treatment.

19. The device of claim 17, wherein the list of health care services includes orthodontic services, dental services, and cosmetic services.

20. The device of claim 19, wherein the digital information for orthodontics services comprises at least one of: a digital model of the patient's malocclusion, financial constraints, treatment length, desired orthodontic function, desired orthodontic appearance, the patient's dental history, the patient's medical history, and acceptable deviations.

21. The device of claim 20, wherein the memory further comprises operational instructions that cause the processing module to determine the treatment objective by:
    determining whether a sufficient amount of the digital information has been received; and
    when a sufficient amount of the digital information has not been received, prompting for further disclosure of the digital information.

22. The device of claim 20, wherein the normalized patient data comprises orthodontics parameters relating to the patient and wherein the memory further comprises operational instructions that cause the processing module to simulate the treatment of the patient by:
    determining whether the simulated treatment result can be obtained using only the orthodontic services;
    when the simulated treatment result cannot be obtained using only orthodontic services, determining whether the simulated treatment result can be obtained through a combination of the orthodontic services and dental services;
    when the simulated treatment result cannot be obtained through a combination of the orthodontic services and the dental services, determining whether the simulated treatment result can be obtained through a combination of at least two of the orthodontic services, the dental services, and oral surgery services;
    when the simulated treatment result cannot be obtained through a combination of at least two of the orthodontic services, the dental services, and the oral surgery services, determining whether the simulated treatment result can be obtained through a combination of at least two of the orthodontic services, the dental services, the oral surgery services, and medical services; and
    when the simulated treatment result cannot be obtained through a combination of at least two of the orthodontic services, the dental services, the oral surgery services, and the medical services, providing an indication that the treatment objectives cannot be obtained.

23. The device of claim 22, wherein the memory further comprises operational instructions that cause the processing module to:
    when the simulated treatment result cannot be obtained using only orthodontic services, provide at least one of: the digital information, the treatment objective, and the orthodontic parameters to a dental resource;
    receive the dental services from the dental resource;
    when the simulated treatment result cannot be obtained through a combination of the orthodontic services and the dental services, provide at least one of: the digital information, the treatment objective, and the orthodontic parameters to an oral surgery resource;
    receive the oral surgery services from the oral surgery resource;
    when the simulated treatment result cannot be obtained through a combination of at least two of the orthodontic services, the dental services, and the oral surgery services, provide at least one of: the digital information, the treatment objective, and the orthodontic parameters to a medical resource; and
    receive the medical services from the medical resource.

24. The device of claim 22, wherein the memory further comprises operational instructions that cause the processing module to:
    when the simulated treatment result cannot be obtained using only the orthodontic services, provide at least one of: the digital information, the treatment objective, and the orthodontic parameters to a dental resource; and
    interact between the dental resource and an orthodontic resource to determine that the combination of orthodontic services and dental services will provide the simulated treatment result; or
    interact between the dental resource and the orthodontic resource to determine that the combination of orthodontic services and dental services will not provide the simulated treatment result.

25. The device of claim 24, wherein the memory further comprises operational instructions that cause the processing module to:
    when the simulated treatment result cannot be obtained using the orthodontic services and the dental services, provide at least one of: the digital information, the treatment objective, and the orthodontic parameters to an oral surgery resource; and
    interact between the dental resource, the orthodontic resource, and the oral surgery resource to determine that the combination of at least two of the orthodontic services, the dental services, and the oral surgery services will provide the simulated treatment result; or
    interact between the dental resource, the orthodontic resource, and the oral surgery resource to determine that the combination of at least two of the orthodontic services, the dental services, and the oral surgery services will not provide the simulated treatment result.

26. The device of claim 24, wherein the memory further comprises operational instructions that cause the processing module to:
    when the simulated treatment result cannot be obtained using the orthodontic services, the dental services, and the oral surgery services, provide at least one of: the digital information, the treatment objective, and the orthodontic parameters to a medical resource; and
    interact between the dental resource, the orthodontic resource, the oral surgery resource, and the medical resource to determine that the combination of at least two of the orthodontic services, the dental services, the oral surgery services, and the medical services will provide the simulated treatment result; or
    interact between the dental resource, the orthodontic resource, the oral surgery resource, and the medical resource to determine that the combination of at least two of the orthodontic services, the dental services, the oral surgery services, and the medical services will not provide the simulated treatment result.

27. The device of claim 22, wherein the memory further comprises operational instructions that cause the processing module to receive a revised treatment objective in response to the providing an indication that the treatment objectives cannot be obtained.

28. A device for generating an oral health care treatment plan, the device comprising:
    a processing module; and
    memory operably coupled to the processing module, wherein the memory includes operational instructions that cause the processing module to: (a) determine at least one treatment objective based on digital information of a patient and selected treatment conditions; (b) generate a normalized treatment plan based on the at least one treatment objective, the digital information and normalized orthodontic parameters; (c) determine whether the normalized treatment plan includes at least one non-orthodontic treatment step; (d) when the normalized treatment plan includes the at least one non-orthodontic treatment step, route the normalized treatment plan to non-orthodontic resource for evaluation based on the non basic treatment step; (e) receive feedback from the non-orthodontic resource regarding the non-orthodontic treatment step; and (f) adjust the normalized treatment plan based on the feedback to produce the oral health care treatment plan when the feedback indicates that the non-orthodontic treatment step is to be modified.

29. The device of claim 28, wherein the memory further comprises operational instructions that cause the processing module to determine the at least one treatment objective by:

providing a user interface to request a plurality of data to produce the digital information;

determining whether a sufficient amount of the plurality of data has been received to produce the normalized treatment plan;

when a sufficient amount of the plurality of data has been received to produce the normalized treatment plan, selecting from a plurality of treatment factors to produce the at least one treatment objective;

generating an exterior appearance model of the patient in accordance with the at least one treatment objective; and when the exterior appearance model is approved, utilizing the at least one treatment objective.

30. The device of claim 29, wherein the memory further comprises operational instructions that cause the processing module to:

when the exterior appearance model is not approved, re-select from the plurality of treatment factors to produce a revised treatment objective;

generate a revised exterior appearance model of the patient in accordance with the revised treatment objective; and when the revised exterior appearance model is approved, utilize the revised treatment objective.

31. The device of claim 28, wherein the non-orthodontic treatment step comprises at least one of a dental service, an oral surgery service, and a medical service.

32. The device of claim 31, wherein the memory further comprises operational instructions that cause the processing module to:

route the normalized treatment plan to a dental resource when the non-orthodontic treatment step requires the dental service;

route the normalized treatment plan to an oral surgery resource when the non-orthodontic treatment step requires the oral surgery service; and route the normalized treatment plan to a medical resource when the non-orthodontic treatment step requires the medical service.

* * * * *